United States Patent
Oei et al.

(10) Patent No.: US 8,538,371 B2
(45) Date of Patent: Sep. 17, 2013

(54) RESUSCITATION TEAM MOBILIZATION SYSTEM, DEVICE AND METHOD

(76) Inventors: Su Kai Oei, Singapore (SG); Jade Poh Joseph Chua, Singapore (SG)

( * ) Notice: Subject to any disclaimer, the term of this patent is extended or adjusted under 35 U.S.C. 154(b) by 354 days.

(21) Appl. No.: 12/744,501

(22) PCT Filed: Dec. 4, 2008

(86) PCT No.: PCT/SG2008/000465
§ 371 (c)(1),
(2), (4) Date: May 25, 2010

(87) PCT Pub. No.: WO2009/075653
PCT Pub. Date: Jun. 18, 2009

(65) Prior Publication Data
US 2010/0248679 A1     Sep. 30, 2010

(30) Foreign Application Priority Data

| Dec. 12, 2007 | (SG) | ................... 200718697-6 |
| Dec. 12, 2007 | (SG) | ................... 200718698-4 |
| Dec. 12, 2007 | (SG) | ................... 200718699-2 |
| Dec. 12, 2007 | (SG) | ................... 200718700-8 |

(51) Int. Cl.
*H04M 11/04*    (2006.01)

(52) U.S. Cl.
USPC ........................................ 455/404.1

(58) Field of Classification Search
USPC ........................................ 455/404.1
See application file for complete search history.

(56) References Cited

U.S. PATENT DOCUMENTS

| 5,942,986 A * | 8/1999 | Shabot et al. ............... 340/7.29 |
| 6,090,056 A | 7/2000 | Bystrom |
| 6,731,962 B1 | 5/2004 | Katarow |
| 7,120,488 B2 | 10/2006 | Nova |
| 7,640,883 B2 * | 1/2010 | Kugel ........................... 116/200 |
| 2001/0001235 A1 * | 5/2001 | Menkedick et al. ........ 340/573.1 |
| 2001/0012923 A1 * | 8/2001 | Christopher ................... 604/48 |
| 2002/0014951 A1 * | 2/2002 | Kramer et al. ................. 340/5.8 |
| 2002/0080037 A1 * | 6/2002 | Dixon et al. ............... 340/573.1 |
| 2003/0206116 A1 * | 11/2003 | Weiner et al. ............ 340/870.28 |
| 2004/0124979 A1 | 7/2004 | Medema |
| 2006/0049936 A1 * | 3/2006 | Collins et al. ............ 340/539.11 |
| 2007/0210917 A1 * | 9/2007 | Collins et al. .............. 340/539.1 |

* cited by examiner

*Primary Examiner* — Nathan Mitchell

(57) ABSTRACT

A resuscitation team mobilization system, device and method are disclosed that minimize the delays frequently associated with responding to a resuscitation emergency. In a preferred embodiment, the system comprises a control station [50]; a to plurality of responder mobilization devices [30]; and a plurality of responder communication devices [70]. In one preferred embodiment, the responder mobilization device [30] comprises a communications unit [32]; a video camera [48] coupled to the communications unit [32]; and a mobilization activation means [34] coupled to the communications unit [32]. During a resuscitation event, the user actuates the mobilization activation means [34]. In response to the actuation of the mobilization activation means [34], the communications unit [32] contacts the control station [50] to mobilize the resuscitation team. In one embodiment, the method comprises the step of detecting a mobilization activation event within the responder mobilization device [30]; and the step of contacting a control station [50] in response to the mobilization activation event.

50 Claims, 12 Drawing Sheets

RESUSCITATION TEAM MOBILIZATION SYSTEM, DEVICE AND METHOD

CROSS REFERENCES TO RELATED APPLICATIONS

This application claims the benefit of the following Singapore patent applications: Singapore patent application number 200718699-2, titled "Responder mobilization device", filed on Dec. 12, 2007; Singapore patent application number 200718697-6, titled "System, device and method for mobilizing a resuscitation team", filed on Dec. 12, 2007; Singapore patent application number 200718698-4, titled "System, device and method for mobilizing a resuscitation team", filed on Dec. 12, 2007; and Singapore patent application number 200718700-8, titled "Responder mobilization device", filed on Dec. 12, 2007, which are all hereby incorporated by reference herein in their entirety.

TECHNICAL FIELD

The disclosed subject matter relates to systems, devices and methods for mobilizing a medical resuscitation team.

BACKGROUND ART

The provision of an effective resuscitation service for people who collapse in a hospital or a medical centre is essential. The passage of time drives all aspects of resuscitation. The final outcomes are determined by the intervals between collapse or onset of the emergency and the delivery of basic and advance interventions. The probability of survival declines sharply with each passing minute of cardiopulmonary compromise. Therefore, response time is critical. A resuscitation team should be able to arrive on the scene of a cardiac arrest within minutes to initiate treatment. The earlier that effective treatment is provided, the more likely the patient is to survive.

The adequate performance of such a service has wide ranging implications with respect to standards of care, risk management and clinical governance. Early resuscitation saves lives.

In one prior art system, when a patient collapses, a first nurse typically shouts for help, then the first nurse checks if the patient is responsive. Meanwhile, a second nurse activates a resuscitation team by shouting into a microphone. The second nurse is typically required to verbally provide the location details to the resuscitation team members. Meanwhile, a third has to push the mobile resuscitation trolley to the collapsed patient's location to commence resuscitation efforts. Unfortunately, this approach is time consuming. Furthermore, if there is a shortage of medical personnel, it is impossible to undertake these actions simultaneously.

In another prior art system, when a patient collapses, a first nurse typically shouts for help, then the first nurse checks if the patient is responsive. Meanwhile, a second nurse has to manually page a resuscitation number or a series of numbers. The second nurse is typically required to manually page the location details to the resuscitation team members. Meanwhile, a third nurse has to push the mobile resuscitation trolley to the collapsed patient's location to commence resuscitation efforts. Again, this approach is time consuming. Furthermore, if there is a shortage of medical personnel, it is impossible to undertake these actions simultaneously.

In yet another prior art system, when a patient collapses, a first nurse typically shouts for help, then the first nurse checks if the patient is responsive. Meanwhile, a second nurse has to manually telephone the hospital operator to trigger a resuscitation alert. The second nurse is typically required to verbally provide the location details to the hospital operator or the resuscitation team members. Meanwhile, a third has to push the mobile resuscitation trolley to the collapsed patient's location to commence resuscitation efforts. This approach is time consuming. Furthermore, if there is a shortage of medical personnel, it is impossible to undertake these actions simultaneously.

The resuscitation trolley typically stores most of the equipment and resuscitation medicines required by a resuscitation team. Each hospital typically uses a standardized trolley. The standard trolley typically has equipment that is standardized throughout the hospital to aid familiarity.

A hospital typically has numerous mobile resuscitation trolleys distributed throughout the hospital and at least one resuscitation team on duty. Although a resuscitation trolley is mobile, it is heavy when fully equipped and is intended only to be pushed over a short distance, typically a few meters. Therefore, each resuscitation trolley serves a small area of the hospital. For example, a hospital ward accomodating ten to twenty patient beds will typically have one mobile resuscitation trolley assigned to the ward. This trolley is usually parked near the ward's nurses' station. The resuscitation trolley can be pushed to the patient's bedside when required. In the event of a resuscitation emergency, the medical personnel is required to push the mobile resuscitation trolley a short distance to the patient's bedside.

A resuscitation team comprises specially trained doctors and nurses who are typically assigned to resuscitation duties for a duty period. The members of the resuscitation team would typically carry a dedicated code pager or mobile phone by which they are activated. During this duty period, the resuscitation team members would normally be expected to continue with their usual clinical responsibilities pending activation.

Each resuscitation team member has a role, and must function as part of the resuscitation team. If activated, and a resuscitation team member is unable to response immediately for whatever reason, the resuscitation team member will have to notify a medical personnel. The medical personnel will then follow a written protocol and manually proceed to activate another suitably trained alternate resuscitation team member. During a resuscitation event, lack of awareness as to whether everyone in the team has arrived at the resuscitation location often results in unnecessary repeated paging or contacting by nurses. Not only is this undesirable because it wastes time and effort sorely needed elsewhere, but it furthermore exposes the resuscitation team members to unnecessary distraction as pagers and mobile phones are unnecessarily activated again and again. Loss of life may result merely because of poor information. As hospitals increase in size and serve thousands of patients, the potential chaos that can result from continuing to manually telephone or to manually page to activate a resuscitation team is apparent.

In a resuscitation emergency, there is a need to mobilize the resuscitation team and to push the resuscitation trolley to the patient's location as soon as possible. Current methods of manually telephoning a hospital operator or manually paging a resuscitation team consumes valuable time in resuscitation emergencies. Therefore, a need exists for a new system, device and method for mobilizing a resuscitation team.

SUMMARY

A resuscitation team mobilization system, device and method are disclosed that minimize the delays frequently associated with responding to a resuscitation emergency. Systems, devices and methods for mobilizing a resuscitation team are provided. In a preferred embodiment of the system for mobilizing a resuscitation team, the system comprises a control station; a plurality of responder mobilization devices capable of establishing bi-directional communications links with the control station; and a plurality of responder communication devices capable of establishing bi-directional communications links with the control station. Each responder mobilization device is securely attached on to a mobile resuscitation trolley. The user of the responder mobilization device is typically a medical personnel.

Each responder mobilization device comprising a communications unit, and a mobilization activation means coupled to the communications unit. The mobilization activation means is actuable by a user to activate the mobilization of the resuscitation team. And the communications unit, in response to the actuation of the mobilization activation means, contacts a control station to mobilize the resuscitation team. Each responder communication device is carried by a resuscitation team member. The control station mobilizes the resuscitation team by communicating mobilization notification messages to the plurality of responder communication devices. The control station comprises a computer system. The computer system is operable by a human operator. The computer system comprises a control unit; a input device coupled to the control unit; a user interface coupled to the control unit; and a communications interface coupled to the control unit. The control unit comprises a processor, and a memory coupled to the processor. The memory functions for storing data and programs. The communications interface is capable of establishing communication links with the plurality of responder mobilization devices and the plurality of responder communication devices. The computer system is capable of receiving, interpreting, validating, and storing all the messages received from, and for generating messages for transmission to, the plurality of responder communication devices and plurality of responder mobilization devices.

In a more preferred embodiment of the system, the communications unit of the responder mobilization device comprises a control unit; a transceiver coupled to the control unit; a speaker means coupled to control unit; a microphone means coupled to the control unit; a display means coupled to the control unit; and an input means coupled to the control unit. The control unit comprises a processor, and a memory coupled to the processor. The memory functions for storing data, selected messages and programs. During the installation of the responder mobilization device on to the resuscitation trolley, the information regarding the parking location of the resuscitation trolley is programmed and stored into the memory as a selected message.

In an even more preferred embodiment of the system, the responder mobilization device further comprises a video camera coupled to the communications unit.

The present invention enables a single medical personnel to push the resuscitation trolley towards the emergency location, and to activate the mobilization of the resuscitation team by actuating the mobilization activation means. The user may actuate the mobilization activation means either before or while pushing the resuscitation trolley towards the collapsed patient's location. In response to the actuation of the mobilization activation means, the communication unit contacts the control station to mobilize the resuscitation team. Each responder mobilization device contacts the control station by establishing a two-way communication link capable of communicating audio, video and data signals. The communication link is configured to provide audio communication between the user of the responder mobilization device and a human operator located at the control station. In a resuscitation emergency, the user is able to push the resuscitation trolley towards the patient's location while simultaneously verbally coordinate with the operator to mobilize the resuscitation team.

In a still even more embodiment of the system, the responder mobilization device contacts the control station by establishing a bi-directional communications link between the responder mobilization device and the control station, and by transmitting a selected message from the responder mobilization device to the control station. The selected message is processed and interpreted by the control station to provide information regarding the general location where the resuscitation trolley is parked. During the mounting of the responder mobilization device on to the resuscitation trolley, the information regarding the parking location of the resuscitation trolley is programmed and stored into the memory as "selected messages". The control station then mobilizes the resuscitation team by communicating mobilization notification messages to the members of the resuscitation team.

In another still even more preferred embodiment of the system, the responder mobilization device further comprises an attendance checking means coupled to the communications unit. The attendance checking means functions for reading the unique identifier tag carried by each resuscitation team member. The attendance checking means after reading each unique identifier tag, sends the tag's unique identifier information to the communications unit for transmission to the control station, whereupon the control station processes the data to determine the attendance status of each member of the resuscitation team. One advantage provided by this aspect of the present invention is that the control station can monitor the attendance status of each resuscitation team member.

The control station comprises a computer system operable by a human operator. The computer system comprises a control unit, a input device, a user interface and a communications interface and a plurality of software programs. The communications interface is capable of establishing communication links with the plurality of responder mobilization devices and the plurality of responder communication devices. The computer system is capable of receiving, interpreting, validating, and storing all the messages received from, and for generating messages for transmission to, the plurality of responder communication devices and plurality of responder mobilization devices. It will be appreciated that a control station can be any emergency control centre. For example, the control station may comprise the hospital operations centre, or any other third-party command centre service. In addition, the control station may provide information and/or instructions to the resuscitation team.

Another aspect of the present invention provides a responder mobilization device for mobilizing a resuscitation team. The responder mobilization device is in the form of a stand-alone unit that is securely mounted on to a resuscitation trolley. In a preferred embodiment, the responder mobilization device comprises a communications unit: a mobilization activation means coupled to the communications unit; and a video camera coupled to the communications unit. During a resuscitation emergency, the user actuates the mobilization activation means to activate the mobilization of the resuscitation team. The communication unit, in response to the actuation of the mobilization activation means, contacts a control station to mobilize the resuscitation team. The communication unit comprises a control unit; a transceiver coupled to the control unit; a speaker means coupled to control unit; a microphone means coupled to the control unit; a display means coupled to the control unit; and an input means coupled to the control unit. The control unit comprises a processor, and a memory coupled to the processor. The memory stores data, selected messages and programs. The selected message contains information regarding the parking location of the resuscitation trolley. The information regarding the parking location is programmed and stored into the memory as "selected messages".

In more preferred embodiment, the responder mobilization device further comprises an attendance checking means coupled to the communications unit. The attendance checking means functions for reading the unique identifier tag carried by each member of the resuscitation team.

The invention provides a method for mobilizing the members of a resuscitation team using a mobile resuscitation trolley mounted responder mobilization device. In a preferred method, the method comprises the step of detecting a mobilization activation event within the responder mobilization device; and the step of contacting a control station in response to the mobilization activation event. The step of detecting a mobilization activation event includes detecting the actuation of the mobilization activation means of the responder mobilization device. The step of contacting the control station comprises the step of establishing a bi-directional communications link between the responder mobilization device and the control station. The bi-directional communications link is capable of communicating audio, video and data signals. In response to the actuation of the mobilization activation means, the responder mobilization device contacts the control station. The control station having a computer system operable by the human operator.

In a more preferred method, the step of contacting the control station further comprises the step of transmitting a selected message to the control station. The control station processes the selected message to determine the parking location of the resuscitation trolley, and initiates a contact sequence by which the resuscitation team members are mobilized. The control station when mobilizing the resuscitation team notifies and directs the resuscitation team to the parking location, and from there, each resuscitation team member can proceed the short distance to the patient's bedside.

The object of the invention is to provide something new.

One advantage of the present invention is that the invention enables a single medical personnel to activate the mobilization of the resuscitation team, and to push the resuscitation trolley towards the patient's location. The user may actuate the mobilization activation means either before or while pushing the resuscitation trolley towards the patient's location.

None of the prior art systems achieve these results in the manner proposed by the present invention.

BRIEF DESCRIPTION OF THE DRAWINGS

The foregoing aspects and many attendant advantages of this invention will become more readily appreciated as the same become better understood by reference to the following detailed description, when taken in conjunction with the accompanying drawings, wherein.

The drawings are intended to depict only typical aspects of the disclosure, and therefore should not be considered as limiting the scope of the disclosure.

DETAILED DESCRIPTION

The present invention relates to a system, device and method for a resuscitation team. According to the present invention, there is provided a system for mobilizing a resuscitation team.

Figure 7:
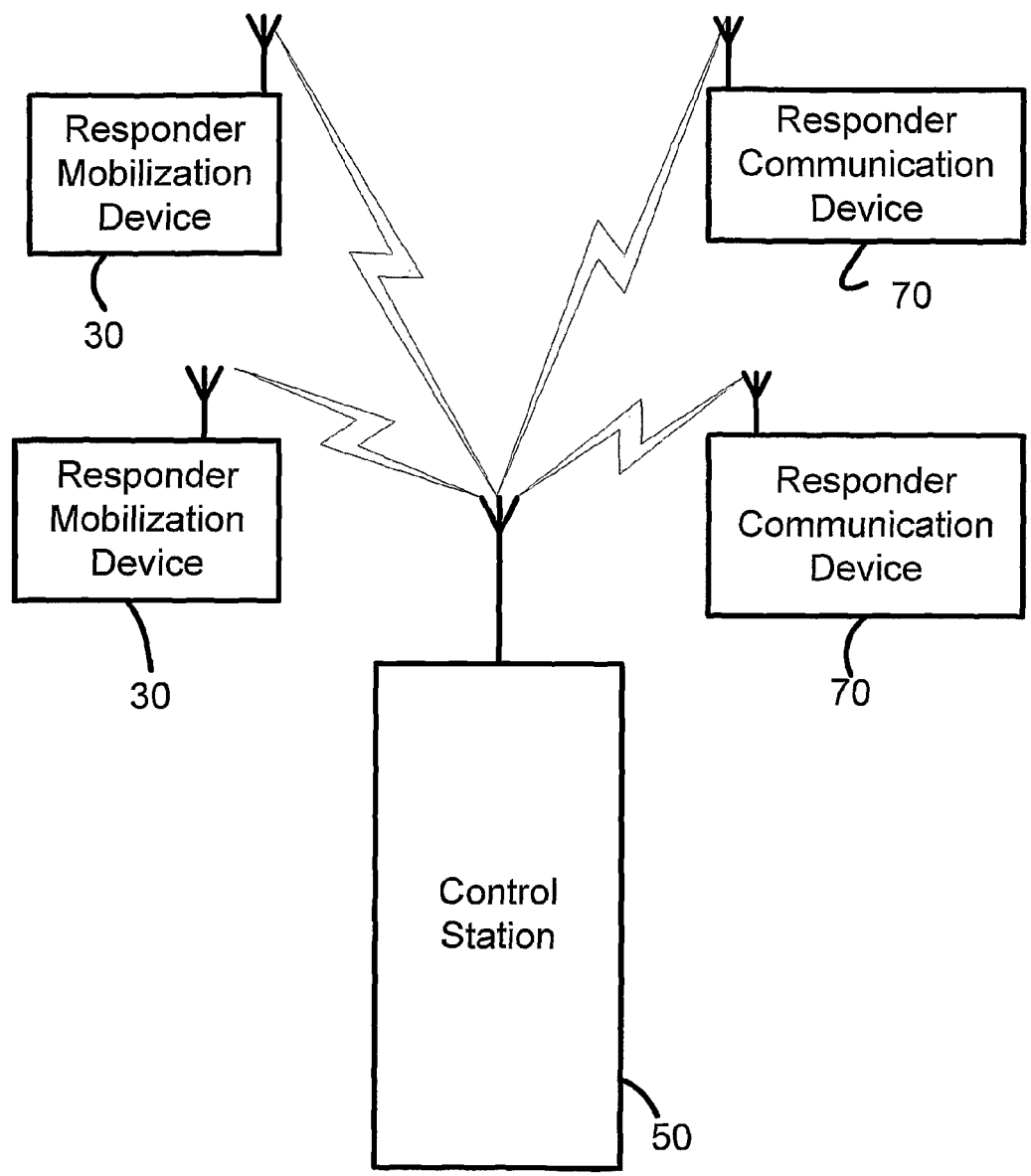
FIG. 7 is a schematic block diagram of a preferred embodiment of the system, the system comprising a control station, a plurality of responder mobilization devices and a plurality of responder communication devices.
Figure 8:
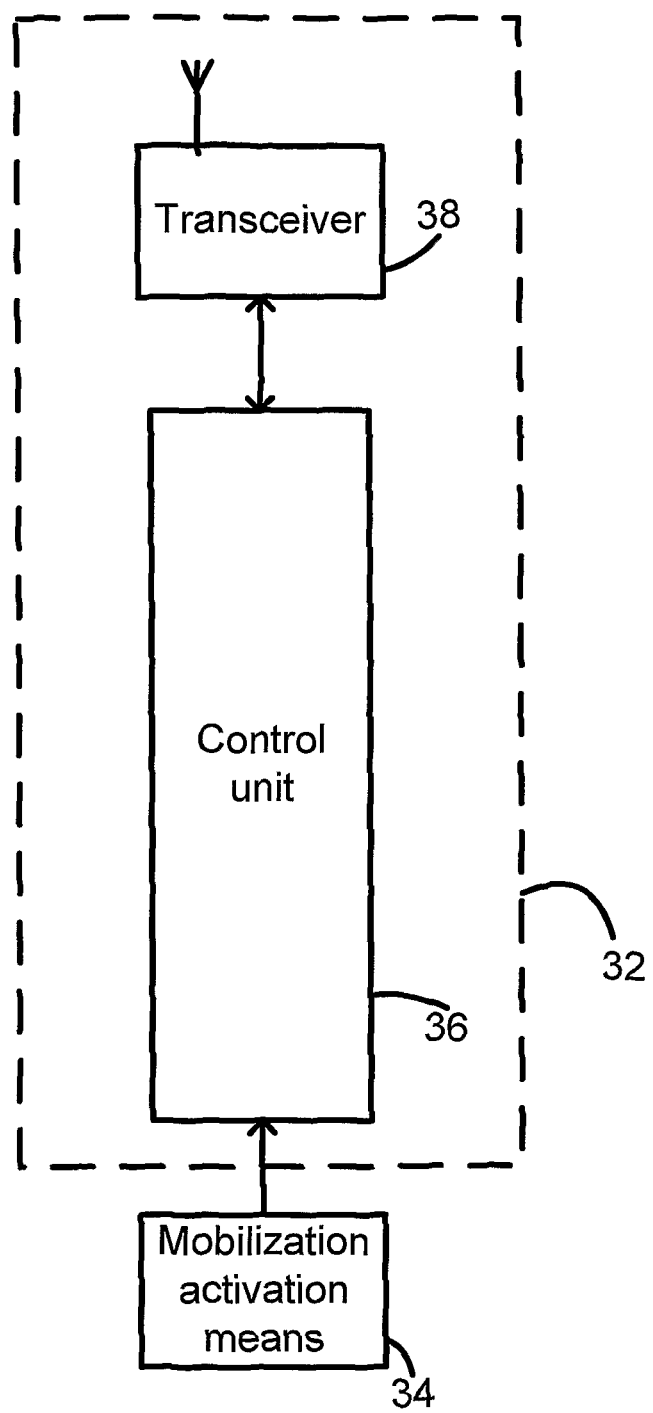
FIG. 8 is a schematic block diagram of the components of an embodiment of the responder mobilization device.

Referring to FIG. 7, in a preferred embodiment of the system, the system comprises a control station 50: a plurality of responder mobilization devices 30 capable of establishing bi-directional communications links with the control station 50; and a plurality of responder communication devices 70 capable of establishing bi-directional communications links with the control station 50. Each responder mobilization device 30 is securely attached on to a mobile resuscitation trolley. The user of the responder mobilization device 30 is typically a medical personnel.

Figure 1:
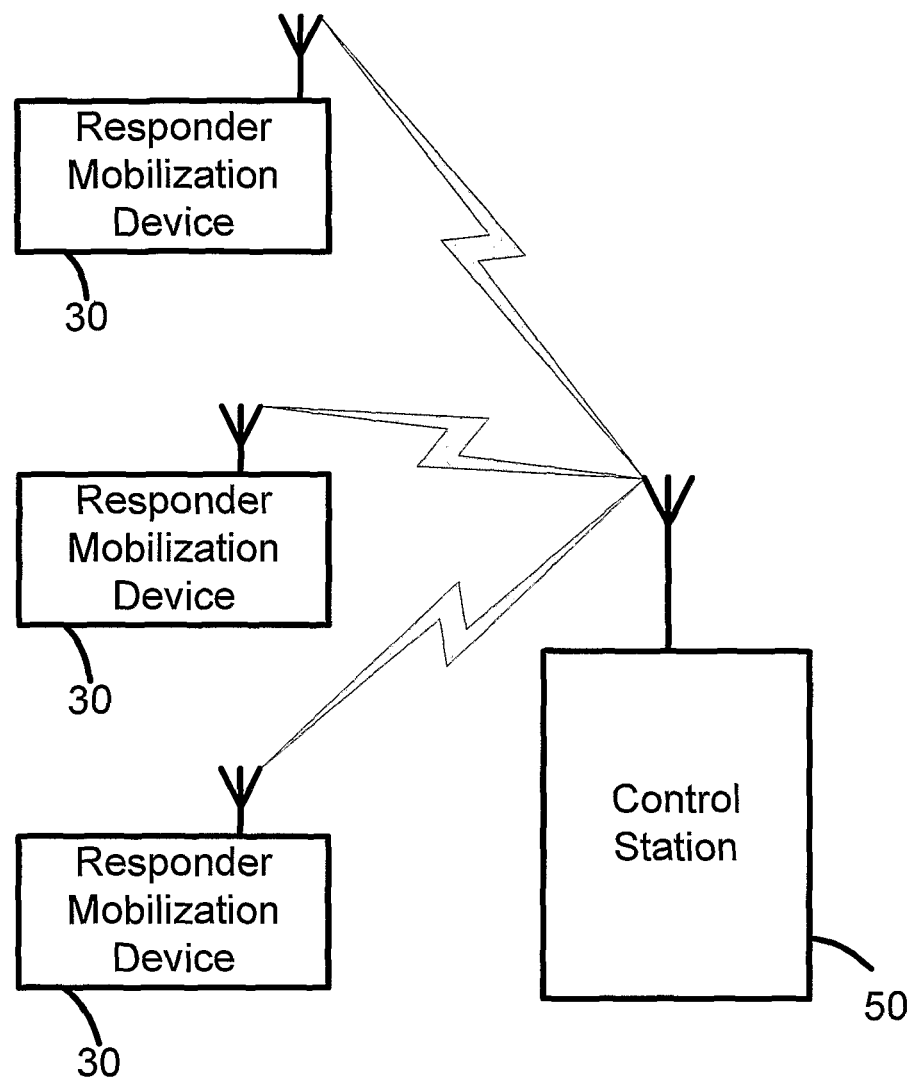
FIG. 1 is a schematic diagram showing a plurality of responder mobilization device capable of establishing communication links with a control station in accordance with one aspect of a system of the present invention.
Figure 2:
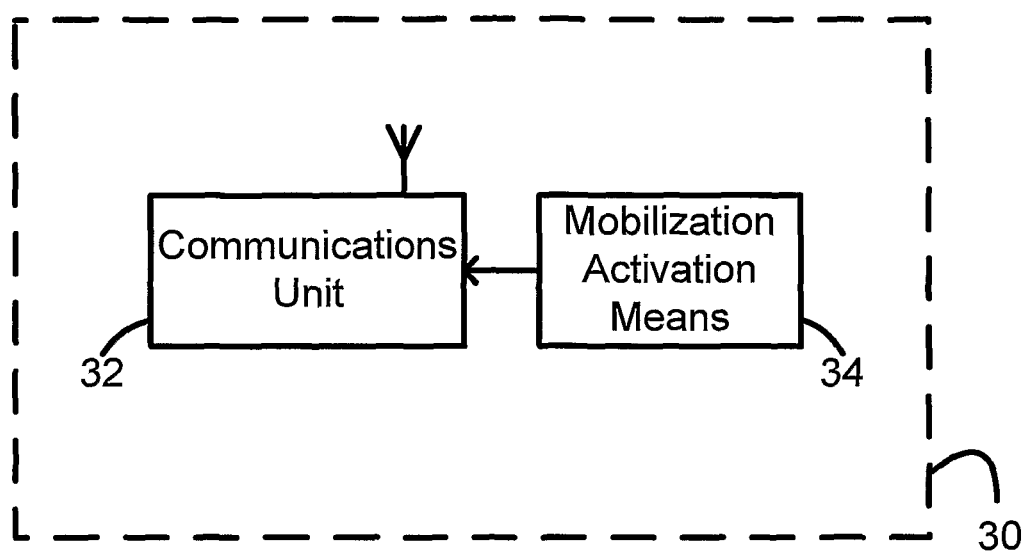
FIG. 2 is a schematic block diagram of the components of an embodiment of the responder mobilization device.

Referring to FIG. 2, each responder mobilization device 30 comprises a communications unit 32, and a mobilization activation means 34 coupled to the communications unit 32. The mobilization activation means 34 is actuable by a user to activate the mobilization of the resuscitation team. The communications unit 32, in response to the actuation of the mobilization activation means 34, contacts a control station 50 to mobilize the resuscitation team. Each responder communication device 70 is carried by a resuscitation team member. The control station 50 mobilizes the resuscitation team by communicating mobilization notification messages to the plurality of responder communication devices 70. The control station 50 comprises a computer system. The computer system is operable by a human operator. The computer system comprises a control unit; a input device coupled to the control unit; a user interface coupled to the control unit; and a communications interface coupled to the control unit. The control unit comprises a processor, and a memory coupled to the processor. The memory serves for storing data and programs. The communications interface is capable of establishing communication links with the plurality of responder mobilization devices 30 and the plurality of responder communication devices 70. The computer system is capable of receiving, interpreting, validating, and storing all the messages received from, and for generating messages for transmission to, the plurality of responder communication devices 70 and plurality of responder mobilization devices 30.

Figure 4:
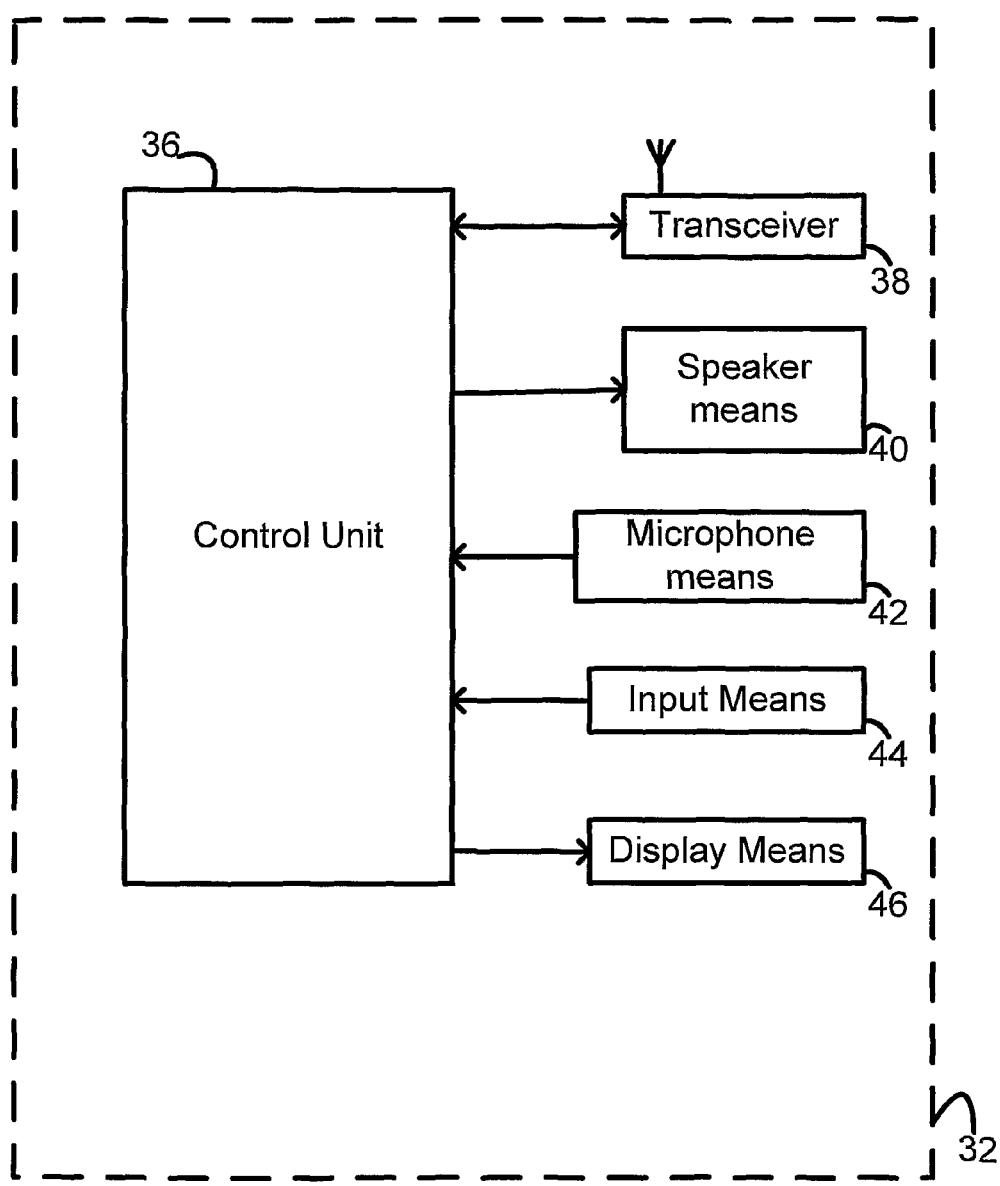
FIG. 4 is a schematic block diagram of the components of the communications unit of an embodiment of the responder mobilization device.

Referring to FIG. 4, in a more preferred embodiment of the system, the communications unit 32 of the responder mobilization device 30 comprises a control unit 36; a transceiver 38 coupled to the control unit 36; a speaker means 40 coupled to control unit 36; a microphone means 42 coupled to the control unit 36; a display means 46 coupled to the control unit 36; and an input means 44 coupled to the control unit 36. The control unit 36 comprises a processor, and a memory coupled to the processor. The memory functions for storing data, selected messages and programs. During the installation of the responder mobilization device 30 on to the resuscitation trolley, the information regarding the parking location of the resuscitation trolley is programmed and stored into the memory as a selected message.

Figure 5:
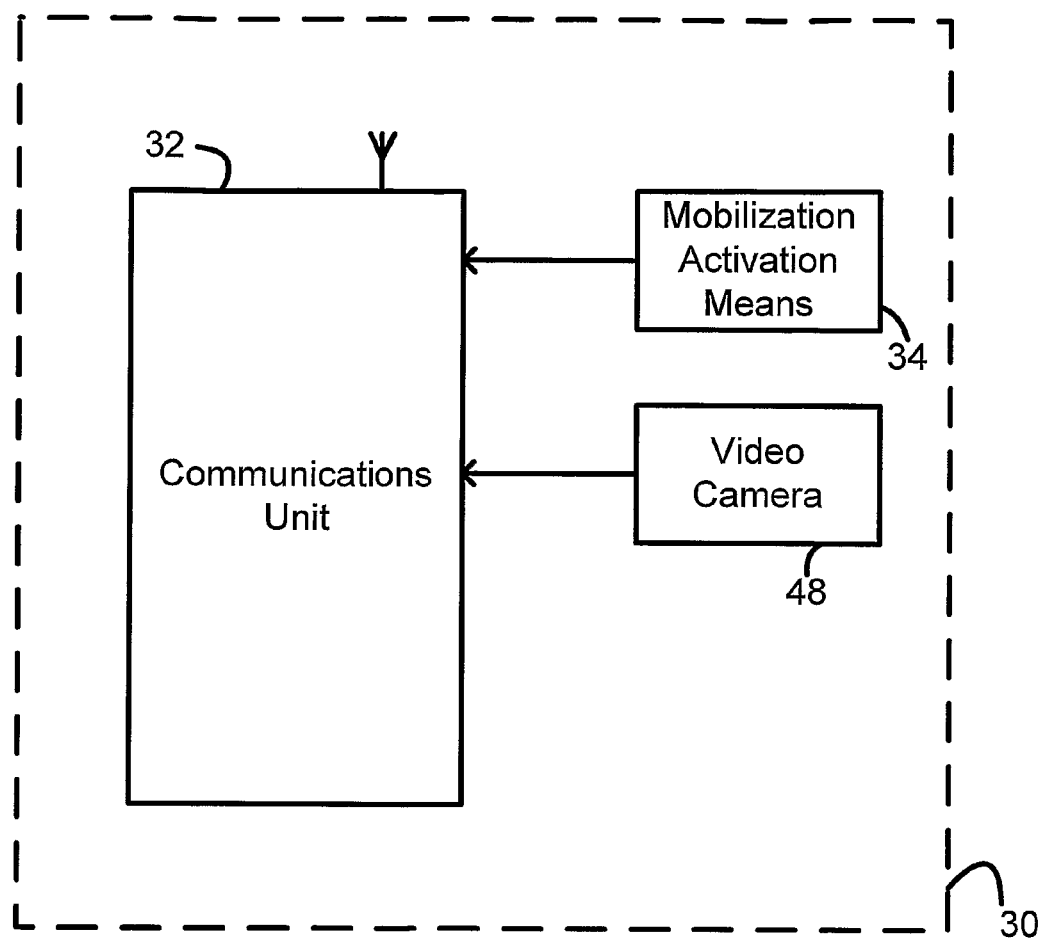
FIG. 5 is a schematic block diagram of the components of another embodiment of the responder mobilization device.

Referring to FIG. 5, in an even more preferred embodiment of the system, the responder mobilization device 30 further comprises a video camera 48 coupled to the communications unit 32.

The present invention enables a single medical personnel to push the resuscitation trolley towards the emergency location, and to activate the mobilization of the resuscitation team by actuating the mobilization activation means 34. The user may actuate the mobilization activation means 34 either before or while pushing the resuscitation trolley towards the collapsed patient's location. In response to the actuation of the mobilization activation means 34, the communication unit 32 contacts the control station 50 to mobilize the resuscitation team. In a still even more preferred embodiment of the system, the responder mobilization device 30 contacts the control station 50 by establishing a two-way communication link capable of communicating audio, video and data signals. The communication link is configured to provide audio communication between the user of the responder mobilization device 30 and a human operator located at the control station 50. In a resuscitation emergency, the user is able to push the resuscitation trolley towards the patient's location while simultaneously verbally coordinate with the operator to mobilize the resuscitation team.

In another still even more preferred embodiment of the system, the responder mobilization device 30 contacts the control station 50 by establishing a bi-directional communications link between the responder mobilization device 30 and the control to station 50, and by transmitting a selected message from the responder mobilization device 30 to the control station 50. The selected message is processed and interpreted by the control station 50 to provide information regarding the general location where the resuscitation trolley is parked. During the mounting of the responder mobilization device 30 on to the resuscitation trolley, the information regarding the parking location of the resuscitation trolley is programmed and stored into the memory as "selected messages". The control station 50 then mobilizes the resuscitation team by communicating mobilization notification messages to the members of the resuscitation team.

In another still even more preferred embodiment of the system, the mobilization activation means 34 comprises one of a button switch and a pull-cord switch.

Figure 6:
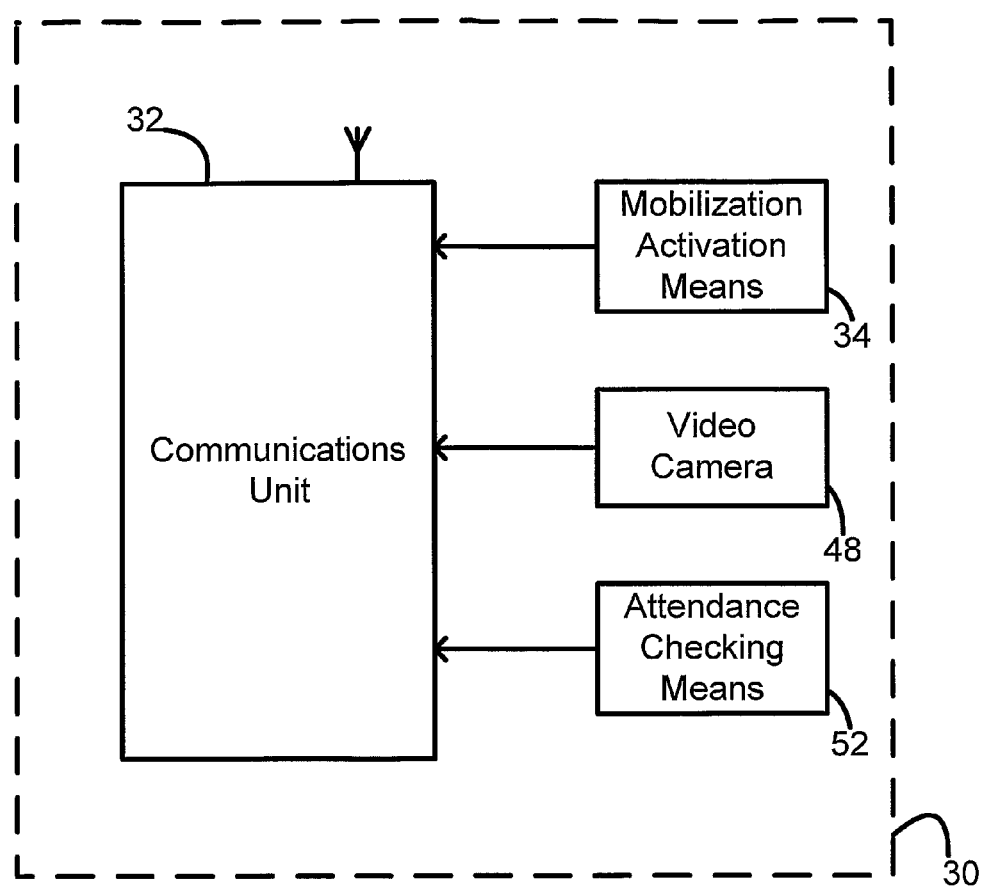
FIG. 6 is a schematic block diagram of the components of yet another embodiment of the responder mobilization device.

Referring to FIG. 6, in another still even more preferred embodiment of the system, the responder mobilization device 30 further comprises an attendance checking means 52 coupled to the communications unit 32. The attendance checking means 52 functions for reading the unique identifier tag carried by each resuscitation team member. The attendance checking means 52 after reading each unique identifier tag, sends the tag's unique identifier information to the communications unit 32 for transmission to the control station 50, whereupon the control station 50 processes the data to determine the attendance status of each member of the resuscitation team.

One advantage provided by this aspect of the present invention is that the control station 50 can monitor the attendance status of each resuscitation team member.

Figure 3:
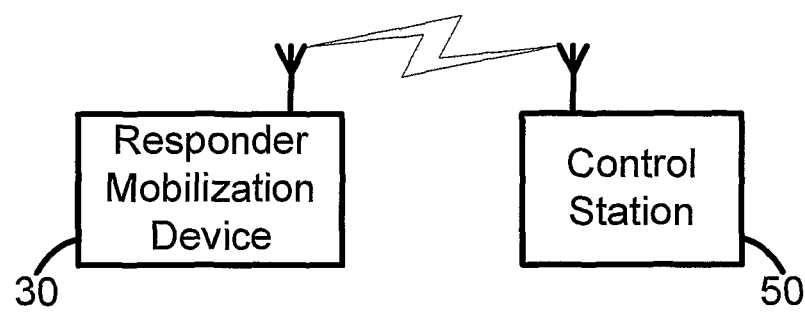
FIG. 3 is a schematic block diagram of a responder mobilization device communicating with a control station in accordance with the present invention.

During a resuscitation emergency, the user actuates the mobilization activation means 34 either before or while pushing the resuscitation trolley towards the patient's location. In response to the actuation of the mobilization activation means 34, the communication unit 32 contacts the control station 50 to mobilize the resuscitation team. As illustrated in FIG. 3, each responder mobilization device 30 contacts the control station 50 by establishing a two-way communication link to capable of communicating audio, video and data signals. For example, in one embodiment, the communications link is configured to provide audio communication between the user of the responder mobilization device 30 and a human operator located at the control station 50. Therefore, using this embodiment, the user is able to push the resuscitation trolley towards the patient's location while simultaneously verbally coordinate with the operator to mobilize the resuscitation team.

The attendance checking means 52 is preferably tag reader. Suitable examples for the tag reader comprise one of a bar code reader and a radio-frequency identification device reader.

In yet another aspect of the invention, each responder communication device 70 is wearable by the resuscitation team member. In yet another aspect of the invention, the responder communication devices 70 are portable information devices comprising cellular phones, a two-way pagers and wireless personal digital assistants.

The responder mobilization device 30 is mounted on to a mobile resuscitation trolley. Therefore, in the preferred embodiment, the bi-directional communications link is preferably a wireless bi-directional communications link. In another preferred embodiment, the communications link is a bi-directional communications link comprising a hardwired segment and a wireless segment. The hardwired segment is preferably coupled to the wireless segment through one or more access points. The access points coupled the hardwired segment to the wireless segment through antennas which transmit a signal to the wireless segment of the communications link. It will be understood to those of ordinary skill in the art that any number of wireless communications systems can be used for the wireless segment of the communications link. Furthermore, any of a number of known hardwired communication systems including local area networks and wide area networks can be used for the hardwired segments. Examples of suitable wired communications media/methods include, but are not limited to, wired digital data networks, such as the Internet or a local area network ("LAN"), co-axial cable, fiber optic cable and the like. Examples of suitable wireless communications media/methods include, but are not limited to, wireless telephony ("cellular") including analog cellular and wireless application protocol ("WAP"). Other suitable wireless communication media/methods include, but are not limited to, wireless digital data networks, such as 802.11 wireless LAN ("WLAN"). Further, some communication methods, either wired or wireless, include Internet protocol ("IP") addressing. Additionally, some embodiments can employ more than one type of hardwired segment and/or more than one type of wireless communication segments. The communications link may comprise only a wireless segment or a combination of a wireless segments and hardwired segments. One skilled in the relevant art will appreciate that additional or alternative communication media/methods may be practiced and are considered within the scope of the present invention.

Once a communications link has been established with control station 50, and the control station 50 has been notified of the resuscitation emergency event, the responder mobilization device 30 may continue transmitting signals/data to and receiving signals/data from the control station 50. The bi-directional communications link and the components of the responder mobilization device 30 allows the control station 50 to transmit and receive patient, medical, location and/or device information to and from the responder mobilization device 30. For example, such information may include, but is not limited to, patient identification data, ECG data, treatment data, operator instructions, emergency instructions, etc. Further, the control station 50 can send video, audio or textural instructions for use by the resuscitation team back to the responder mobilization device 30, which can then pass the instructions on to a user via its user interface. Accordingly, the control station 50 can remotely and in real-time assist the resuscitation team, thus saving valuable time and resources.

Furthermore, as the responder mobilization device 30 reads each unique identifier tag, the responder mobilization device 30 transmits confirmation of the member's attendance to the control station 50, which in turn, may record such data for auditing. Alternatively, as the responder mobilization device 30 fails to read any unique identifier tag within an allowed response time period, the control station 50 may mobilize alternate resuscitation team members. The control station 50 and the responder mobilization device 30 may exchange such information and instructions until the communication link is terminated.

Another aspect of the present invention provides a responder mobilization device 30 for mobilizing a resuscitation team. FIG. 2 is a schematic block diagram of an embodiment of the responder mobilization device 30. The responder mobilization device 30 is in the form of a stand-alone unit that is securely attached on to a resuscitation trolley.

In a preferred embodiment, the responder mobilization device 30 comprises a communications unit 32; a mobilization activation means 34 coupled to the communications unit 32; and a video camera 48 coupled to the communications unit 32. During a resuscitation emergency, the user actuates the mobilization activation means 34 to activate the mobilization of the resuscitation team. The communication unit 32, in response to the actuation of the mobilization activation means 34, contacts a control station 50 to mobilize the resuscitation team. Referring to FIG. 4, the communications unit 32 of the responder mobilization device 30 comprises a control unit 36; a transceiver 38 coupled to the control unit 36; a speaker means 40 coupled to control unit 36; a microphone means 42 coupled to the control unit 36; an input means 44 coupled to the control unit 36; and a display means 46 coupled to the control unit 36. The control unit 36 comprises a processor, and a memory coupled to the processor. The memory functions for storing data, selected messages and programs. A suitable example for the display means 46 is a liquid crystal display (LCD) capable of producing text and graphics displays. In one embodiment of the present invention, the control station can send visual (e.g., video, graphical, textual, etc.) or aural instructions back to the responder mobilization device 30 to assist the resuscitation team. Accordingly, the control station 50 can remotely and in real-time assist the members of the resuscitation team in the emergency treatment of the patient. The responder mobilization device 30 can transmit video images captured by the video camera 48 to the control station 50. One advantage of this embodiment is is that the control station 50 can record resuscitation team activities for auditing purposes and/or for quality control purposes.

As shown in FIG. 3, in a more preferred embodiment, the responder mobilization device 30 contacts the control station 50 by establishing a two-way communication link capable of communicating audio, video and data signals.

In another more preferred embodiment, the responder mobilization device 30 contacts the control station 50 by establishing a wireless bi-directional communication link with the control station 50, and by transmitting a selected message to the control station 50. The selected message is processed and interpreted by the control station 50 to determine the parking location of the resuscitation trolley. One advantage of this embodiment is that the user does not have to verbally communicate the parking location of the resuscitation trolley to the control station operator.

In another more preferred embodiment, the mobilization activation means 34 comprises one of a button switch and a pull-cord switch. During a resuscitation event, the user, either before or while pushing the resuscitation trolley, can pull the pull-cord switch to initiate the mobilization of the resuscitation team.

In another more preferred embodiment, the responder mobilization device 30 further comprises an attendance checking means 52 coupled to the communications unit 32. The attendance checking means 52 functions for reading the unique identifier tag carried by each resuscitation team member. The attendance checking means 52 after reading each unique identifier tag, sends the tag's unique identifier to the communications unit 32 for transmission to the control station 50, whereupon the control station 50 processes the data to determine the attendance status of each resuscitation team member. The attendance checking means 52 is preferably tag reader. Suitable examples for the tag reader comprise one of a bar code reader and a radio-frequency identification device reader.

Furthermore, in difficult resuscitation emergencies, the resuscitation team may need to consult with medical colleagues. Under the existing prior art system, the resuscitation team member often has to resort to leaving the patient's bedside to use a land line public telephone network or to using a cellular link. Another advantage of the present invention is that the bi-directional audio/video/data communications link and the components of the responder mobilization device 30 (e.g., the display means 46, microphone 42, speaker means 40, video camera 48 described above), enables a medical consultant at the control station 50 to assist the resuscitation team to treat the patient in real-time. More specifically, instructions for delivering therapy, treating the patient, etc., may be sent from the control station 50 to the responder mobilization device 30 in the form of voice instructions, text messages, video images, graphical illustrations, etc. In addition, instructions generated by pre-programmed, protocol driven instruction sets may be sent or prompted for display by the responder mobilization device 30. Thus, the invention allows resuscitation team members to consult with a medical colleague located at the control station.

In a preferred second embodiment of the system, the system comprises a control station 50; a plurality of responder mobilization devices 30 capable of establishing bi-directional communications links with the control station 50; and a plurality of responder communication devices 70 capable of establishing bi-directional communications links with the control station 50. Each responder mobilization device 30 comprises a communications unit 32, and a mobilization activation means 34 coupled to the communications unit 32. The communications unit 32 comprises a control unit 36 and a transceiver 38. The control unit 36 comprises a processor, a memory means coupled to the processor, programs stored on the memory, and data. The transceiver 38 is coupled to the control unit 36. The transceiver 38 has a unique code. The transceiver 38 is capable of establishing a bi-directional communications link with the control station 50. In use, actuation of the mobilization activation means 34 by the user activates the responder mobilization device 30 and causes the control unit 36 to generate a mobilization activation message and to send the message to the transceiver 38. The mobilization activation message comprises the unique code. The transceiver 38 transmits the mobilization activation message to the control station 50, and the control station 50 upon receipt of the mobilization activation message, processes and interprets the mobilization activation message, and mobilizes the resuscitation team. Suitable examples for the mobilization activation means 34 are a switch, a pull-cord switch and an accelerometer.

In a more preferred second embodiment of the system, the responder mobilization device 30 further comprises a mobilization cancellation means 54 coupled to the control unit 36. In use, the mobilization cancellation means 54 is operable by the user to generate a mobilization cancellation message to indicate the cancellation of the mobilization activation. The transceiver 38 transmits the mobilization cancellation message to the control station 50, and the control station 50 upon receipt of the mobilization cancellation message, processes and interprets the mobilization cancellation message, and notifies the resuscitation team of the cancellation of the mobilization.

In an even more preferred second embodiment of the system, the responder mobilization device 30 further comprises an attendance checking means 52 coupled to the control unit 36. The attendance checking means 52 reads the unique identifier tag carried by each resuscitation team member. The attendance checking means 52 after reading the unique identifier tag, sends the tag's unique identifier information to the transceiver 38 for transmission to the control station 50. In one embodiment, the attendance checking means 52 is a tag reader. Suitable examples for the tag reader comprises one of a bar code reader and a radio-frequency identification device reader.

In yet another aspect of the system of the invention, the computer system of the control station 50 has software for generating a mobilization notification messages. In yet another aspect of the system of the invention, computer system of the control station 50 has software for generating a mobilization notification messages, software for processing and interpreting the unique identifier information from each unique identifier tag, software for determining and recording the response times for each resuscitation team member, software for identifying which member of the resuscitation team has not responded, and software for determining the need to mobilize an alternate resuscitation member.

In preferred second embodiment of the responder mobilization device 30, the responder mobilization device 30 comprises a communications unit 32; a mobilization activation means 34 coupled to the communications unit 32; and a video camera 48 coupled to the communications unit 32. The communication unit 32 comprises a control unit 36; a transceiver 38, having a unique code, coupled to the control unit 36; a speaker means 40 coupled to control unit 36; a microphone means 42 coupled to the control unit 36; a display means 46 coupled to the control unit 36; and an input means 44 coupled to the control unit 36. The control unit 36 comprises a processor, and a memory coupled to the processor. The memory stores data, selected messages and programs. The transceiver 38 having a unique code. The mobilization activation means 34 when actuated by a user causes the transceiver 38 to establish a bi-directional communications link with a control station 50, and further causes the control unit 36 to generate a mobilization activation message, and to send the message to the transceiver 38. The mobilization activation message comprises the unique code information. The transceiver 38 transmits the mobilization activation message to the control station 50. The control station 50 receives, processes and interprets the mobilization activation message and mobilizes the resuscitation team.

During the installation of the responder mobilization device 30 on to the resuscitation trolley, the transceiver's unique code information and the parking location of the resuscitation trolley are administratively linked. Thereafter, the control station 50 can process and interpret the unique code information to determine the parking location of the resuscitation trolley. The control station 50 when mobilizing the resuscitation team notifies and directs the resuscitation team to the parking location, and from there, each resuscitation team member can proceed the short distance to the patient's bedside.

Figure 9:
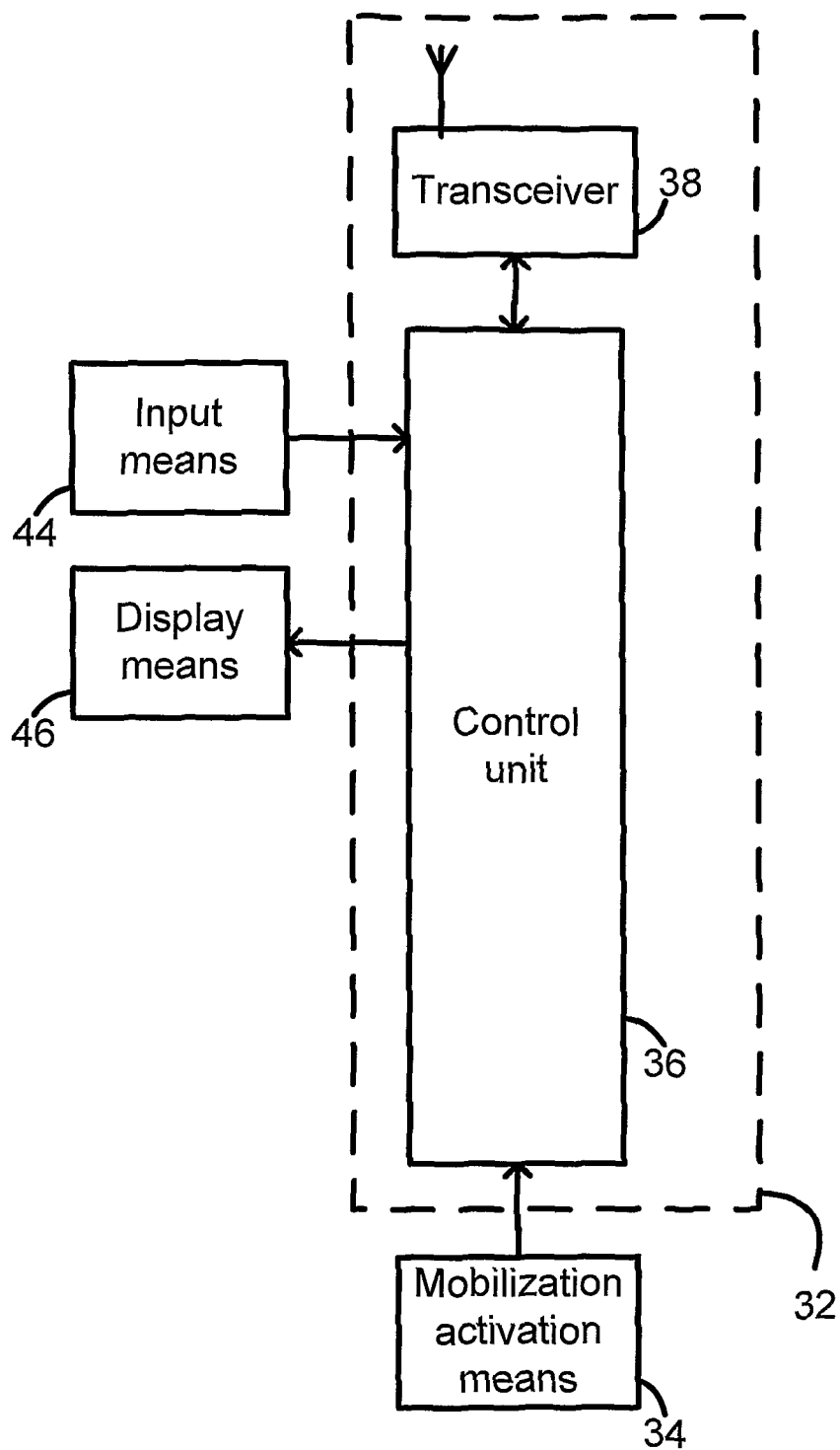
FIG. 9 is a schematic block diagram of the components of more preferred second embodiment of the responder mobilization device.
Figure 10:
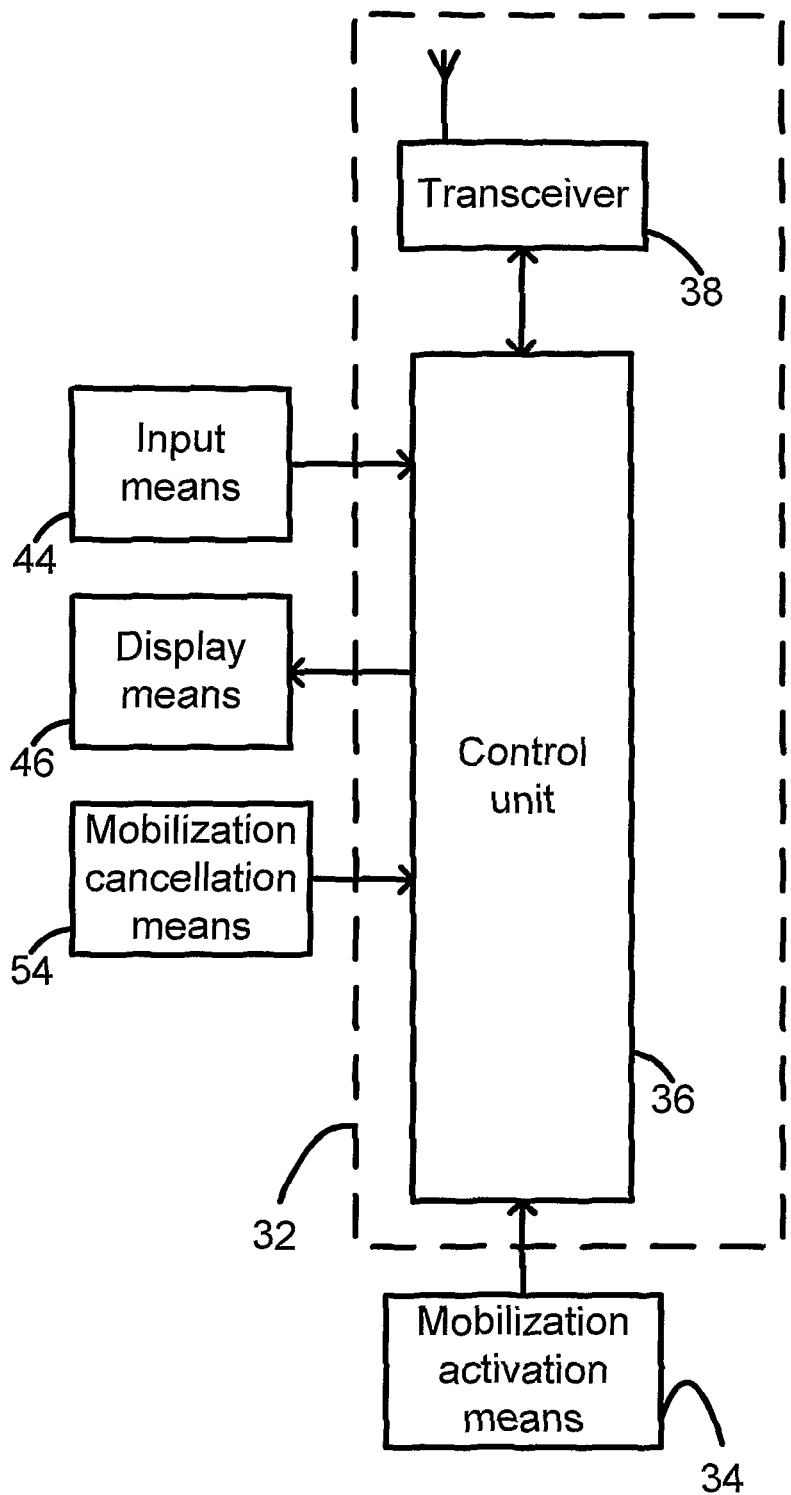
FIG. 10 is a schematic block diagram of the components of an even more preferred second embodiment of the responder mobilization device.

Referring to FIG. 9, in more preferred second embodiment of the responder mobilization device 30, the responder mobilization device 30 further comprises an input means 44 and a display means 46. The input means 44 is coupled to the control unit 36. The input means 44 functions for entering data. The display means 46 is coupled to the control unit 36. The display means 46 functions for displaying data and messages. One advantage of this embodiment is that the bi-directional communications link and the components of this embodiment allows the responder mobilization device 30 to transmit and receive patient, medical, location and/or device information to and from the control station 50. For example, such information may include, but is not limited to, patient identification data, ECG data, treatment data, operator instructions, emergency instructions, etc Referring to FIG. 10, in even more preferred second embodiment, the responder mobilization device 30 further comprises a mobilization cancellation means 54 coupled to the control unit 36. The mobilization cancellation means 54 is operable by the user to generate a mobilization cancellation message. The mobilization cancellation message indicates cancellation of the mobilization activation. The mobilization cancellation message is sent from the control unit 36 to the transceiver 38 for transmission to the control station 50, and whereupon the control station 50 processes and interprets the mobilization cancellation message and notifies the resuscitation team of the cancellation of the mobilization.

Figure 11:
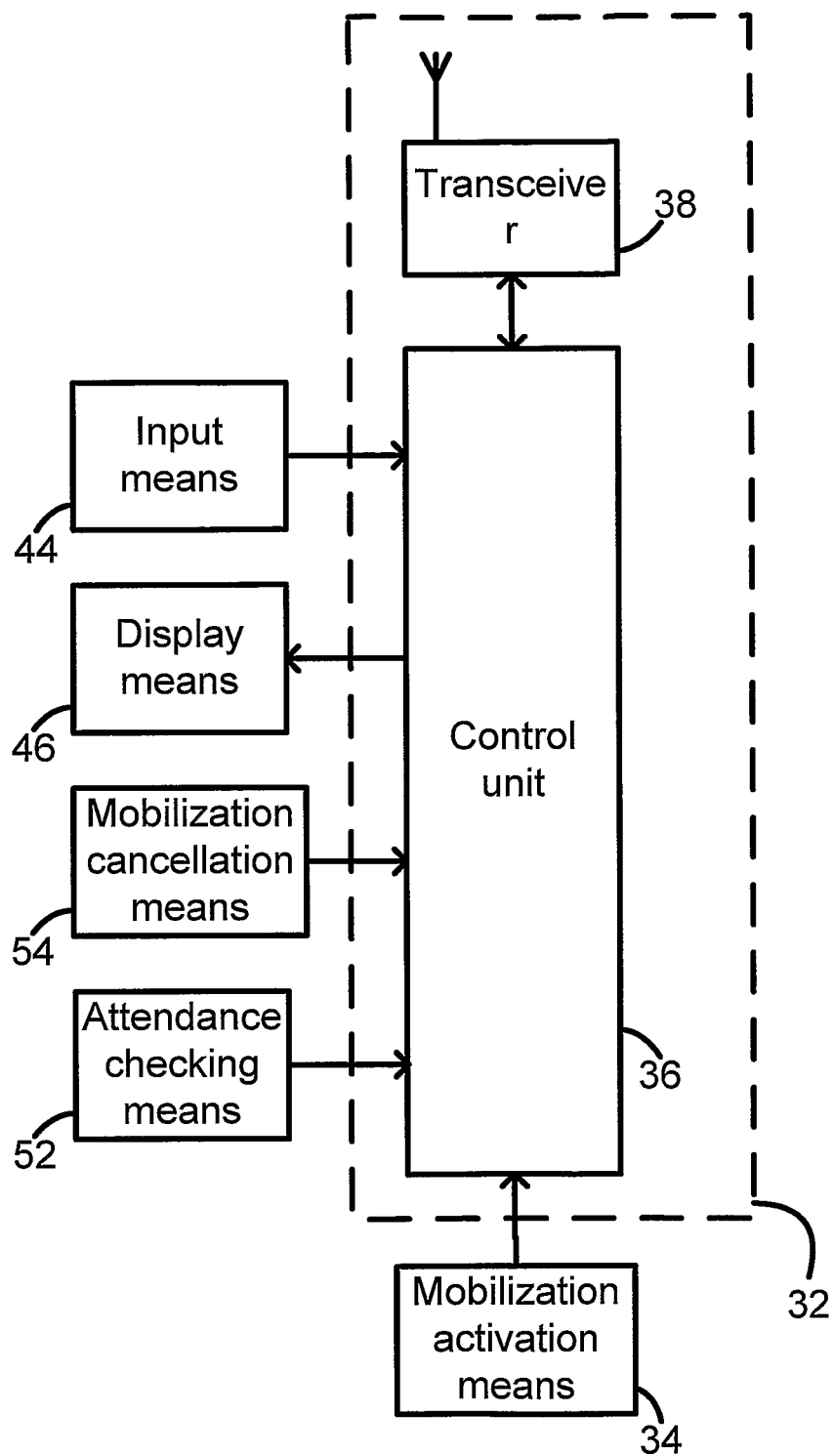
FIG. 11 is a schematic block diagram of the components of a still even more preferred second embodiment of the responder mobilization device.

Referring to FIG. 11, in a still even more preferred second embodiment, the responder mobilization device 30 further comprises an attendance checking means 52 coupled to the control unit 36. The attendance checking means 52 functions for reading a unique identifier tag carried by each member of the resuscitation team. The attendance checking means 52 after reading the tag, sends the unique identifier information to the control unit 36, and the control unit 36 sends the unique identifier information to the transceiver 38 for transmission to the control station 50. The control station 50 processes and interprets the unique identifier information to determine the attendance status of the resuscitation team member. One advantage of this embodiment is that it enables the control station 50 to track the attendance of each resuscitation team member. The control station 50 may also record the attendance data for auditing. In one embodiment, the attendance checking means 52 is a tag reader. Suitable examples of tag readers are a bar code reader and a radio-frequency identification device reader.

Figure 12:
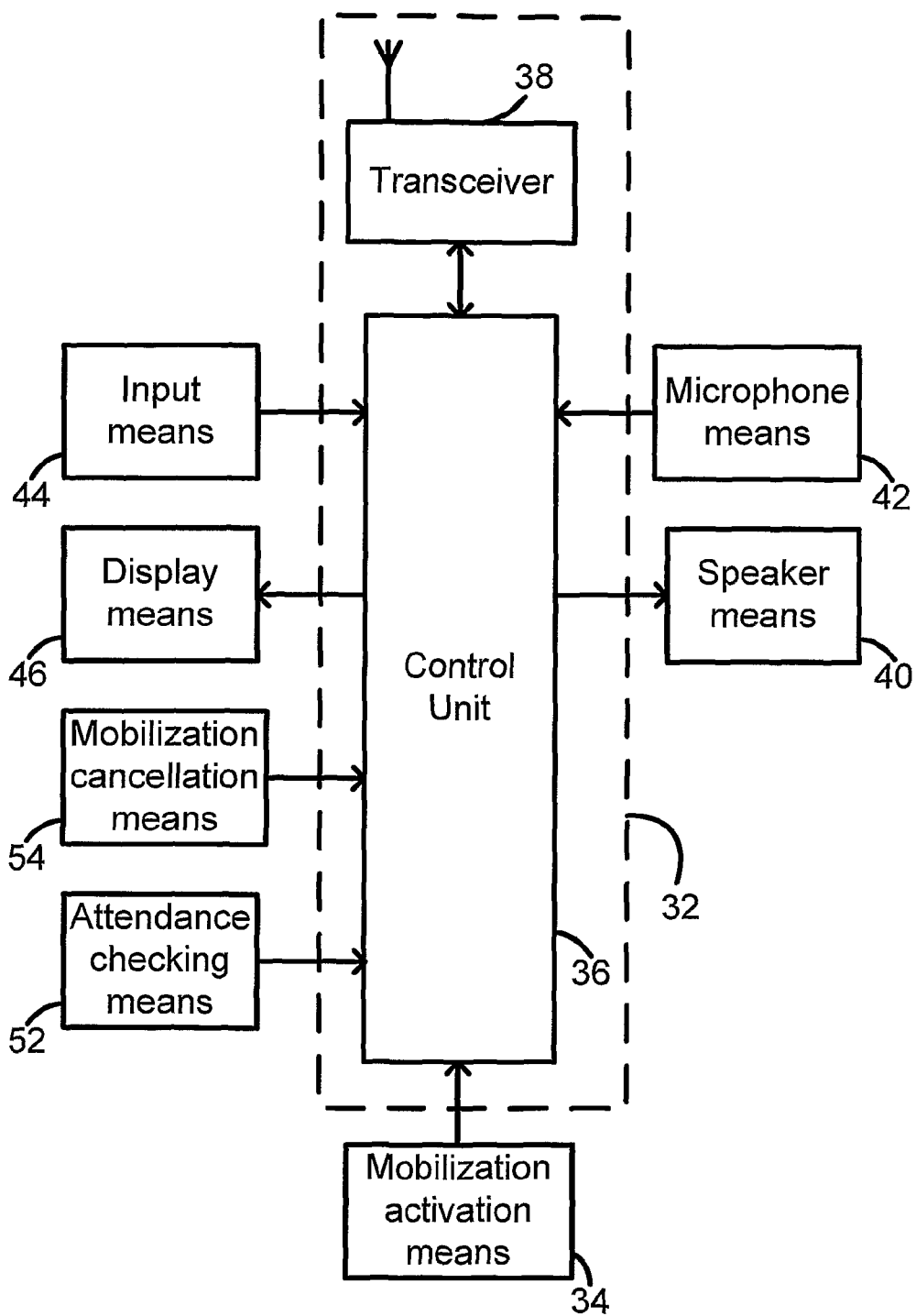
FIG. 12 is a schematic block diagram of the components of yet still even more preferred second embodiment of the responder mobilization device.

Referring to FIG. 12, in yet still even more preferred second embodiment, the responder mobilization device 30 further comprises a microphone means 42 and a speaker means 40. The speaker means 40 is coupled to the control unit 36. The microphone means 42 is coupled to the control unit 36. The bi-directional communications link and the components of this embodiment allows the responder mobilization device 30 to transmit and receive patient, medical, location and/or device information to and from the control station 50. For example, such information may include, but is not limited to, patient identification data, ECG data, treatment data, operator instructions, emergency instructions, etc. Further, the control station 50 can send video, audio or textural instructions for use by the resuscitation team back to the responder mobilization device 30. Accordingly, the medical personnel stationed at the control station 50 can remotely and in real-time assist the resuscitation team, thus saving valuable time and resources.

The responder mobilization device 30 is securely mounted on to a mobile resuscitation trolley. Therefore, in the preferred embodiment, the bi-directional communications link is preferably a wireless bi-directional communications link. The bi-directional communications link is capable of video, audio and data transmission. In another preferred embodiment, the responder mobilization device 30 establishes the bi-directional communications link with the control station 50 through a communications network, the communications network having a wireless segment and a hardwired segment. In yet another preferred embodiment, the communications link is a bi-directional communications link comprising a hardwired segment and a wireless segment. The hardwired segment is preferably coupled to the wireless segment through one or more access points. The access points coupled the hardwired segment to the wireless segment through antennas which transmit a signal to the wireless segment of the communications link. It will be understood to those of ordinary skill in the art that any number of wireless communications systems can be used for the wireless segment of the communications link. Furthermore, any of a number of known hardwired communication systems including local area networks and wide area networks can be used for the hardwired segments. Examples of suitable wired communications media/methods include, but are not limited to, wired digital data networks, such as the Internet or a local area network ("LAN"), co-axial cable, fiber optic cable and the like. Examples of suitable wireless communications media/methods include, but are not limited to, wireless telephony ("cellular") including analog cellular and wireless application protocol ("WAP"). Other suitable wireless communication media/methods include, but are not limited to, wireless digital data networks, such as 802.11 wireless LAN ("WLAN"). Further, some communication methods, either wired or wireless, include Internet protocol ("IP") addressing. Additionally, some embodiments can employ more than one type of hardwired segment and/or more than one type of wireless communication segments. The communication link may comprise only a wireless segment or a combination of a wireless segments and hardwired segments. One skilled in the relevant art will appreciate that additional or alternative communication media/methods may be is practiced and are considered within the scope of the present invention.

Once a bi-directional communications link has been established with control station 50, and the control station 50 has been notified of a resuscitation event, the responder mobilization device 30 may continue transmitting signals/data to and receiving signals/data from the control station 50.

In one embodiment of the responder mobilization device 30, the display means 40 is an LCD display screen. In another embodiment of the responder mobilization device 30, the mobilization activation means 34 is a switch. In another embodiment of the responder mobilization device 30, the mobilization activation means 34 is an accelerometer. The accelerometer functions for detecting a rapid acceleration of the medical resuscitation trolley. The accelerometer generates a mobilization activation message when a rapid acceleration is recorded by the accelerometer.

Now that various device embodiments have been described, the methods used by the responder mobilization device 30 to mobilize the resuscitation team will be discussed.

The method of the invention commences when a mobilization activation event occurs. For purposes of the present example, it will be assumed that a patient requires emergency resuscitation, and accordingly, the mobilization activation event is the actuation of the mobilization activation means 34 of the responder mobilization device 30.

The invention provides a method for mobilizing the members of a resuscitation team using a mobile resuscitation trolley mounted responder mobilization device 30. In a preferred method, the method comprises the step of detecting a mobilization activation event within the responder mobilization device 30; and the step of contacting a control station 50 in response to the mobilization activation event. The step of detecting a mobilization activation event includes detecting the actuation of the mobilization activation means 34 of the responder mobilization device 30. The mobilization activation event occurs as a result of a user-initiated action, such as depressing a button switch with which the responder mobilization device 30 is equipped. In response to the detection of a mobilization activation event, e.g. actuation of the mobilization activation means 34 of the responder mobilization device 30, the responder mobilization device 30 contacts the control station 50. The step of contacting the control station comprises the step of establishing a bi-directional communications link between the responder mobilization device 30 and the control station 50, wherein the bi-directional communications link is capable of communicating audio, video and data signals. In response to the actuation of the mobilization activation means 34, the responder mobilization device 30 contacts the control station 50. The control station 50 having a computer system operable by the human operator.

In a more preferred method, the step of contacting the control station 50 further comprises the step of transmitting a selected message to the control station 50. The control station 50 processes the selected message to determine the parking location of the resuscitation trolley, and initiates a contact sequence by which the resuscitation team members are mobilized. The control station 50 when mobilizing the resuscitation team notifies and directs the resuscitation team to the parking location, and from there, each resuscitation team member can proceed the short distance to the patient's bedside.

In an even more preferred method, the method further comprises the steps of receiving and processing said selected message at said control station 50; displaying said selected message in a convenient format for use by said human operator at said control station 50; and initiating a contact sequence by which the resuscitation team members are mobilized.

In a still even more preferred method, the method further comprises the steps of reading the unique identifier tag carried by each resuscitation team member; and transmitting unique identifier information to said control station 50.

In yet still even more preferred method, the method further comprises the steps of processing the unique identifier information at said control station 50; identifying the resuscitation team members who have responded within an allowed time period; determining the resuscitation team members who have not responded within an allowed response time period; and generating and transmitting mobilization notification messages from said control station 50 to an alternate resuscitation team member's responder communication device 70.

In another aspect of the method, the step of contacting the control station 50 includes establishing a communications link with the control station 50, and generating and transmitting a mobilization activation message to the control station 50. The mobilization activation message comprises the transceiver's unique code information.

In still another aspect of the method, the method further comprises the steps of receiving and processing the mobilization activation message at the control station 50 to provide information regarding the parking location of the resuscitation trolley, and notifying the resuscitation team members. In one aspect, the step of notifying comprises the step of initiating a contact sequence by which resuscitation team members are mobilized.

In still another aspect of the method, the step of notifying further comprises the step of generating and transmitting mobilization notification messages from the control station 50 to the plurality of responder communication devices 70.

In yet still another aspect of the method, the method further comprises the steps of reading the unique identifier tag carried by each resuscitation team member; and transmitting said tag's unique identifier information to said control station 50.

In still yet still another aspect of the method, the method further comprises the steps of processing said tag's unique identifier information at said control station 50; identifying resuscitation team members who have not responded within an allowed time period; and generating and transmitting mobilization notification messages from said control station 50 to said alternate resuscitation team member's responder communication device 70.

While the preferred embodiments of the invention have been illustrated and described, it will be appreciated that various changes can be made therein without departing from the scope of the invention.

We claim:

1. A system for mobilizing a resuscitation team, said system comprising:
a control station;
a plurality of responder mobilization devices capable of establishing bi-directional communications links with said control station, each responder mobilization device is securely attached on to a mobile resuscitation trolley, each responder mobilization device comprising a communications unit; and a mobilization activation means coupled to said communications unit; and a plurality of responder communication devices capable of establishing bi-directional communications links with said control station,
wherein said mobilization activation means is actuable by a user to activate the mobilization of said resuscitation team,
wherein said communications unit, in response to the actuation of said mobilization activation means, contacts a control station to mobilize said resuscitation team,
wherein each responder communication device is carried by a resuscitation team member,
wherein said control station mobilizes said resuscitation team by communicating mobilization notification messages to said plurality of responder communication devices,
wherein said control station comprises a computer system, said computer system is operable by a human operator, said computer system comprising: a control unit, said control unit comprising a processor, and a memory coupled to said processor, said memory for storing data and programs; a input device coupled to said control unit; a user interface coupled to said control unit; and a communications interface coupled to said control unit,
wherein said communications interface is capable of establishing communication links with said plurality of responder mobilization devices and said plurality of responder communication devices, and
wherein said computer system is capable of receiving, interpreting, validating, and storing all the messages received from, and for generating messages for transmission to, said plurality of responder communication devices and plurality of responder mobilization devices.

2. The system as claimed in claim 1, wherein said communications unit of said responder mobilization device comprises:
a control unit, said control unit comprising a processor, and a memory coupled to said processor, said memory for storing data, selected messages and programs;
a transceiver coupled to said control unit; a speaker means coupled to control unit;
a microphone means coupled to said control unit; a display means coupled to said control unit; and an input means coupled to said control unit.

3. The system as claimed in claim 2, wherein said responder mobilization device further comprises: a video camera coupled to said communications unit.

4. The system as claimed in claim 3, wherein said responder mobilization device contacts said control station by establishing a bi-directional communications link with said control station, said bi-directional communications link is capable of communicating audio, video and data signals.

5. The system as claimed in claim 3, wherein said responder mobilization device contacts said control station by establishing a bi-directional communications link with said control station, and by transmitting a selected message to said control station, and wherein said selected message is processed and interpreted by said control station to provide information regarding the parking location of the resuscitation trolley.

6. The system as claimed in claim 3, wherein said mobilization activation means comprises one of a button switch and a pull-cord switch.

7. The system as claimed in claim 3, wherein said responder mobilization device further comprises: an attendance checking means coupled to said communications unit, said attendance checking means for reading the unique identifier tag carried by each member of said resuscitation team, wherein said attendance checking means after reading said unique identifier tag, sends said tag's unique identifier information to said communications unit for transmission to said control station.

8. The system as claimed in claim 7, wherein said attendance checking means is a tag reader, said tag reader comprising one of a bar code reader and a radio-frequency identification device reader.

9. The system as claimed in claim 1, wherein said responder communication device is wearable by a member of said resuscitation team.

10. The system as claimed in claim 9, wherein said responder communication devices are portable information devices comprising cellular phones, a two-way pagers and wireless personal digital assistants.

11. A responder mobilization device for mobilizing a resuscitation team, said device comprising:
a communications unit;
a video camera coupled to said communication unit;
and a mobilization activation means coupled to said communications unit, wherein
said mobilization activation means is actuable by a user to initiate the mobilization of said resuscitation team,
wherein said communications unit, in response to the actuation of said mobilization activation means, contacts a control station to mobilize said resuscitation team, and
wherein said communications unit comprises:
a control unit, said control unit comprising a processor, and a memory coupled to said processor, said memory for storing data, selected messages and programs:
a transceiver coupled to said control unit;
a speaker means coupled to control unit;
a microphone means coupled to said control unit;
a display means coupled to said control unit; and
an input means coupled to said control unit.

12. The device of claim 11, wherein said device contacts said control station by establishing a bi-directional communications link with said control station, said bi-directional communications link is capable of communicating audio, video and data signals.

13. The device of claim 11, wherein said device contacts said control station by establishing a bi-directional communications link with said control station, and by transmitting a selected message to said control station, and wherein said selected message is processed and interpreted by said control station to provide information regarding the parking location of the resuscitation trolley.

14. The device of claim 11, wherein said mobilization activation means comprises one of a button switch and a pull-cord switch.

15. The device of claim 11, wherein said responder mobilization device further comprises: an attendance checking means coupled to said communications unit, said attendance checking means functions for reading the unique identifier tag carried by each resuscitation team member, and wherein said attendance checking means after reading said unique identifier tag, sends the unique identifier information to said communications unit for transmission to said control station.

16. The device of claim 15, wherein said attendance checking means is a tag reader, said tag reader comprising one of a bar code reader and a radio-frequency identification device reader.

17. A method for mobilizing a resuscitation team using a mobile resuscitation trolley mounted responder mobilization device, said method comprising the steps of:
detecting an mobilization activation event within said responder mobilization device; and
contacting a control station in response to said mobilization activation event, said control station having a computer system operable by said human operator, wherein the step of detecting a mobilization activation event includes detecting the actuation of the mobilization activation means of said responder mobilization device, and wherein said step of contacting said control station comprises the step of;
establishing a bi-directional communications link between said responder mobilization device and said control station, said bi-directional communications link is capable of communicating audio, video and data signals.

18. The method of claim 17, wherein said step of contacting said control station further comprises the step of: transmitting a selected message from said responder mobilization device to said control station.

19. The method of claim 18, further comprising the steps of:
receiving and processing said selected message at said control station; displaying said selected message in a convenient format for use by said human operator at said control station; and initiating a contact sequence by which the resuscitation team members are mobilized.

20. The method of claim 19, further comprising the steps of: reading the unique identifier tag carried by each resuscitation team member; and transmitting unique identifier information to said control station.

21. The method of claim 20, further comprising the steps of:
processing the unique identifier information at said control station;
identifying the resuscitation team members who have responded within an allowed time period; determining the resuscitation team members who have not responded within an allowed response time period; and generating and transmitting mobilization notification messages from said control station to an alternate resuscitation team member's responder communication device.

22. The system as claimed in claim 1, wherein said communications unit comprises:
a control unit, said control unit comprising a processor, a memory means coupled to said processor, programs stored on said memory, and data; a transceiver coupled to said control unit, said transceiver having a unique code, said transceiver capable of establishing a bi-directional communications link with said control station.

23. The system as claimed in claim 22, wherein actuation of said mobilization activation means by a user activates said device and causes said control unit to generate a mobilization activation message and to send said message to said transceiver, said mobilization activation message comprising said unique code, wherein said transceiver transmits said mobilization activation message to said control station, and wherein said control station upon receipt of said mobilization activation message, processes and interprets said mobilization activation message, and mobilizes said resuscitation team.

24. The system as claimed in claim 23, wherein said responder mobilization device further comprises a mobilization cancellation means coupled to said control unit, wherein said mobilization cancellation means is operable to generate a mobilization cancellation message, said mobilization cancellation message indicating cancellation of the mobilization activation, wherein said transceiver transmits said mobilization cancellation message to said control station, and wherein said control station upon receipt of said mobilization cancellation message, processes and interprets said mobilization cancellation message, and notifies said resuscitation team of the cancellation of the mobilization.

25. The system as claimed in claim 24, wherein said responder mobilization device further comprises: an attendance checking means coupled to said control unit, said attendance checking means for reading a unique identifier tag carried by each resuscitation team member, wherein said attendance checking means after reading said unique identifier tag, sends said tag's unique identifier information to said transceiver for transmission to said control station.

26. The system as claimed in claim 25, wherein said attendance checking means is a tag reader, said tag reader comprising one of a bar code reader and a radio-frequency identification device reader.

27. The system as claimed in claim 26, wherein said mobilization activation means is a switch.

28. The system as claimed in claim 26, wherein said mobilization activation means is an acceleratometer.

29. The system as claimed in claim 1, wherein said programs comprises software for generating a mobilization notification messages.

30. The system as claimed in claim 29, wherein said software programs further comprises: software for processing and interpreting the unique identifier information from each unique identifier tag; software for determining and recording the response times for each resuscitation team member; software for identifying which member of the resuscitation team has not responded; and software for determining the need to mobilize an alternate resuscitation member.

31. The device of claim 11, wherein said communications unit comprises: a control unit, said control unit comprising a processor, a memory means coupled to said processor, programs stored on said memory, and data; and a transceiver coupled to said control unit, said transceiver having a unique code.

32. The device of claim 31, wherein said mobilization activation means when actuated by a user activates said device and causes the transceiver to establish a bi-directional communications link with a control station, wherein said mobilization activation means when actuated further causes said control unit to generate a mobilization activation message, and to send said message to said transceiver, said mobilization activation message comprising the unique code information, wherein said transceiver transmits said mobilization activation message to said control station, and wherein said control station receives, processes and interprets said mobilization activation message and mobilizes said resuscitation team.

33. The device of claim 32, further comprising: an input means coupled to said control unit, said input means for entering data; and a display means coupled to said control unit, said display means for displaying data and messages.

34. The device of claim 33, further comprising: an mobilization cancellation means coupled to said control unit, said mobilization cancellation means operable to generate a mobilization cancellation message, said mobilization cancellation message indicating cancellation of the mobilization activation,
wherein said transceiver transmits said mobilization cancellation message to said control station, and wherein said control station upon receipt of said mobilization cancellation message, processes and interprets said mobilization cancellation message, and notifies said resuscitation team of the cancellation of the mobilization.

35. The device of claim 34, wherein said device further comprises:
an attendance checking means coupled to said control unit, said attendance checking means for reading a unique identifier tag carried by each resuscitation team member, wherein said attendance checking means after reading said unique identifier tag, sends said tag's unique identifier information to said control unit, and said control unit sends said unique identifier information to said transceiver for transmission to said control station, and wherein said control station processes and interprets said unique identifier information to determine the attendance status of each member of the team.

36. The device of claim 35, wherein said attendance checking means is a tag reader, said tag reader comprising one of a bar code reader and a radio-frequency identification device reader.

37. The device of claim 35, wherein said mobilization cancellation means is a switch.

38. The device of claim 35, further comprising: a speaker means coupled to said control unit; and a microphone means coupled to said control unit.

39. The device of claim 38, wherein said bi-directional communications link is capable of video, audio and data transmission.

40. The device of claim 39, wherein said device establishes said bi-directional communications link with said control station through a communications network, said communications network having a wireless segment and a hardwired segment.

41. The device of claim 40, wherein said display means is an LCD display screen.

42. The device of claim 41, wherein said mobilization activation means is an accelerometer, said accelerometer for detecting rapid acceleration of the medical resuscitation trolley, said accelerometer generates a mobilization activation message when a rapid acceleration is recorded by said accelerometer.

43. The device of claim 41, wherein said mobilization activation means is a switch.

44. The method of claim 17, in which contacting said control station includes establishing a communications link with said control station, and generating and sending the mobilization activation message to said control station.

45. The method of claim 44, wherein said mobilization activation message comprises: the transceiver's unique code information.

46. The method of claim 45, further comprising the steps of:
receiving and processing said mobilization activation message at said control station to provide information regarding the parking location of the resuscitation trolley; and
notifying the resuscitation team members.

47. The method of claim 46, wherein said step of notifying comprises the step of initiating a contact sequence by which said resuscitation team members are mobilized.

48. The method of claim 47, wherein said step of notifying further comprises the step of generating and transmitting mobilization notification messages from said control station to said plurality of responder communication devices.

49. The method of claim 48, further comprising the steps of:
reading the unique identifier tag carried by each resuscitation team member; and
transmitting said tag's unique identifier information to said control station.

50. The method of claim 49, further comprising the steps of:
- processing said tag's unique identifier information at said control station;
- identifying resuscitation team members who have not responded within an allowed time period; and generating and transmitting mobilization notification messages from said control station to said alternate resuscitation team member's responder communication device.

* * * * *